US011666639B2

(12) United States Patent
Seidensticker et al.

(10) Patent No.: US 11,666,639 B2
(45) Date of Patent: *Jun. 6, 2023

(54) RECOVERY DIETARY SUPPLEMENT

(71) Applicant: SOCIETE DES PRODUITS NESTLE S.A., Vevey (CH)

(72) Inventors: Kurt Seidensticker, Chicago, IL (US); Matt Aporta, Chicago, IL (US); Corey Friese, Chicago, IL (US); Angela Skubal, Chicago, IL (US)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/891,178

(22) Filed: Jun. 3, 2020

(65) Prior Publication Data

US 2020/0376091 A1 Dec. 3, 2020

Related U.S. Application Data

(60) Provisional application No. 62/856,588, filed on Jun. 3, 2019.

(51) Int. Cl.
| | |
|---|---|
| *A61K 38/39* | (2006.01) |
| *A61K 31/185* | (2006.01) |
| *A61K 31/375* | (2006.01) |
| *A61K 31/51* | (2006.01) |
| *A61K 31/525* | (2006.01) |
| *A61K 31/455* | (2006.01) |
| *A61K 31/675* | (2006.01) |
| *A61K 31/519* | (2006.01) |
| *A61K 33/06* | (2006.01) |
| *A61K 33/30* | (2006.01) |
| *A61K 33/04* | (2006.01) |
| *A61K 33/00* | (2006.01) |
| *A61K 9/14* | (2006.01) |
| *A23L 33/175* | (2016.01) |
| *A23L 33/155* | (2016.01) |
| *A23L 33/00* | (2016.01) |
| *A61K 31/198* | (2006.01) |

(52) U.S. Cl.
CPC ............ *A61K 38/39* (2013.01); *A23L 33/155* (2016.08); *A23L 33/175* (2016.08); *A23L 33/30* (2016.08); *A61K 9/14* (2013.01); *A61K 31/185* (2013.01); *A61K 31/198* (2013.01); *A61K 31/375* (2013.01); *A61K 31/455* (2013.01); *A61K 31/51* (2013.01); *A61K 31/519* (2013.01); *A61K 31/525* (2013.01); *A61K 31/675* (2013.01); *A61K 33/00* (2013.01); *A61K 33/04* (2013.01); *A61K 33/06* (2013.01); *A61K 33/30* (2013.01); *A23V 2002/00* (2013.01)

(58) Field of Classification Search
CPC ............................ A61K 38/39; A23V 2002/00
See application file for complete search history.

(56) References Cited

U.S. PATENT DOCUMENTS

| | | | | |
|---|---|---|---|---|
| 2005/0191385 A1* | 9/2005 | Amato | ............ | A61K 38/17 426/23 |
| 2009/0117208 A1* | 5/2009 | Abe | ............ | A61K 31/401 424/719 |
| 2011/0217393 A1* | 9/2011 | Grise | ............ | A61K 36/45 424/732 |
| 2018/0161296 A1* | 6/2018 | Dunstan | ............ | A61K 31/198 |

FOREIGN PATENT DOCUMENTS

| | | | | |
|---|---|---|---|---|
| CN | 108208827 A | * | 6/2018 | ............ A23L 33/10 |
| CN | 108684999 A | * | 10/2018 | ............ A23L 2/38 |
| EP | 2923583 A1 | | 9/2015 | |
| KR | 20030013836 A | | 2/2003 | |
| WO | 2004032653 A1 | | 4/2004 | |

OTHER PUBLICATIONS

Revel (Women's Recovery + Collagen and Coconut Water—BCAAs with Collagen & Coconut Water for Women—Bodybuilding.com, oldest customer review date: May 24, 2019) (Year: 2019).*
Vital (Vital Proteins, Bone Broth Collagen, Beef, 10 oz (285 g)—iHerb, date first available: Jun. 1, 2017) (Year: 2017).*
CN108208827A, Escapenet English Translation, downloaded in Aug. 2021 (Year: 2021).*
What eats cows?, http://www.whateats.com/what-eats-a-cow, publication date Mar. 30, 2010 (Year: 2010).*
G. Wu et al (Composition of free and peptide-bound amino acids in beef chuck, loin, and round cuts, J. Anim. Sci. 2016.94:2603-2613) (Year: 2016).*
Marjorie Porter Penfield (Changes in Tenderness and Collagen of Beef Semitendinosus Muscle Heated at Two Rates, PhD diss., University of Tennessee, 1973) (Year: 1973).*
Health Benefits Times, What is Beef broth, Beef broth facts, downloaded in Feb. 2022 (Year: 2022).*
"Licorice", Licorice, What is Licorice made of?, downloaded in Jun. 2022 (Year: 2022).*
CN108684999A, Google English Translation, downloaded in Jun. 2022 (Year: 2022).*
European Patent Office Communication for Application No. 20818906.8-1105 / 3976088 PCT/US2020/035838, dated Jan. 3, 2023, 14 pages.

* cited by examiner

*Primary Examiner* — Mark V Stevens
*Assistant Examiner* — Alparslan Asan
(74) *Attorney, Agent, or Firm* — K&L Gates LLP

(57) ABSTRACT

The present invention is directed to a method of replacing collagen broken down during physical activity using a novel dietary supplement. The supplement composition of the present invention comprises collagen, glutamine, taurine, and, optionally, the nine essential amino acids. The uptake of collagen is enhanced using this combination of components to levels substantially near the pre-workout levels.

7 Claims, No Drawings

RECOVERY DIETARY SUPPLEMENT

RELATED APPLICATIONS

This application claims priority from U.S. Provisional Application No. 62/856,588 filed on Jun. 3, 2019, which is incorporated by reference herein.

BACKGROUND

Connective tissue is a major part of muscles, tendons, ligaments, cartilage, and bones. It is the second biggest mass and organ of the body and is important for physical performance. Connective tissue contains mainly collagen structures, which provides bones, tendons, and ligaments structure. Connective tissue contains a matrix of very flexible collagen strings, which is highly stabilized by cross-linking the gelatin-like strings of collagen with pyridinoline (PD) and deoxypyrolidine (DPD). PD and DPD are present only in mature collagen and not in freshly built collagen. In the process of making collagen, collagen strings are first built and then cross-linked with PD and DPD.

During training, athletes break down the collagen in their muscles and joints. Urinary analysis of athletes highlight that PD and DPD are excreted in the urine during and after training, which is indicative of collagen breakdown.

Compositions comprising collagen with branched amino acids have previously been tested to try to replace the collagen lost during strenuous physical activity. Researchers have identified that when supplemented with collagen peptides in combination with arginine and branched-chain amino acids, amino acid levels increase to optimal levels in athletes leading to a 54% reduction in injury in weekend warriors and 67% reduction in injury of muscles, tendons, and ligaments in professional athletes.

However, there remains a need to increase the uptake of collagen along with address other nutrient deficiencies, including the replacement of other amino acids, vitamins, minerals, and electrolytes lost during strenuous physical activity. The present invention resolves this deficiency and enhances the uptake of collagen peptides based on the components of the composition.

SUMMARY

The present invention is directed to a dietary supplement composition comprising collagen peptides, glutamine, and taurine. The composition may further include nine essential amino acids: leucine, isoleucine, valine, lysine, phenylalanine, threonine, tryptophan, histidine, and methionine. The composition of the present invention may be in the form of a solution, suspension, powder, gel, or a liquid. Liquid compositions in turn may be in the form of a concentrated liquid composition, to which a diluent is added, or to fully-diluted liquid compositions, such as ready-to-drink ("RTD") compositions.

In one embodiment, the collagen is present in an amount of about 30 to 60 weight percent of the composition, glutamine is present in an amount of about 2 to about 3.5 weight percent of the composition, and taurine is present in an amount of about 0.2 to about 0.5 weight percent of the composition.

Alternatively, the dietary supplement composition may contain collagen in an amount of about 40-55 weight percent of the composition, glutamine in an amount of about 2.75-3.0 weight percent of the composition, and taurine in an amount of about 0.3-0.45 weight percent of the composition. In another embodiment, collagen is present in an amount of about 50-55 weight percent of the composition, glutamine is present in an amount of about 2.75-3.0 weight percent of the composition, and taurine is present in an amount of about 0.4-0.42 weight percent of the composition.

The present invention also may be described by the amount of collagen, glutamine, and taurine in a standard serving, where the standard serving size is 36-38 grams or, for diluted compositions, 24 fluid ounces. In one embodiment of the present invention, the amount of collagen in the composition is about 10-30 grams/serving, the amount of glutamine in the composition is about 0.5-1.5 grams/serving, and the amount of taurine in the composition is about 0.1-0.2 grams/serving.

Additional components of the composition may include coconut water, electrolytes, such as sodium, potassium, magnesium, and zinc, selenium, and vitamins. The vitamins may include Vitamin B1, Vitamin B2, Vitamin B3, Vitamin B6, Vitamin B5, folate, Vitamin C, and Vitamin D.

The compositions of the present invention are intended to replace collagen broken down during physical activity. Administration of the composition to a patient in need thereof may bring post-collagen levels of the athlete to within 0-5%, 0-10%, or 0-15% of the collagen levels pre-workout or PD and DPD levels within 1%, 2%, 5%, or 10% of the pre-workout levels.

DETAILED DESCRIPTION OF THE INVENTION

The present invention relates to a dietary supplement composition that may be consumed as a meal or as a meal supplement to maintain collagen levels in the body, which help to support muscles, joints, tendons, and ligaments. The compositions of the present invention comprise collagen, preferably in the form of collagen peptides, in combination with glutamine and taurine, and preferably with the essential amino acids and branched-chain amino acids. The composition may be used in the form of a liquid, solution, suspension, powder, or gel. If in powder form, the powder preferably is mixed in a soluble liquid prior to administration as directed. Compositions in the form of liquids include concentrated liquid compositions, to which a diluent is added, as well as fully-diluted liquid compositions, such as ready-to-drink ("RTD") compositions.

Collagen is present in the composition in an amount of about 30 to 60 weight percent of the composition, about 40 to 55 weight percent of the composition, or about 50 to 55 weight percent of the composition. Alternatively, in a standard serving size of 36-38 gram or 24 fluid ounces, collagen may be present in the composition in an amount of about 10-30 grams/serving, about 15-25 grams/serving, about 17-23 grams/serving, or about 20 grams/serving. In a preferred embodiment, collagen may be present in the composition in an amount of about 20 grams/serving.

Collagen is a protein and may be present in any available form in the composition. However, the present invention preferably uses collagen peptides. Collagen peptides may be sourced from any known source, including but not limited to, beef, chicken, fish, eggshell membrane, and chicken egg whites.

Glutamine is present in the composition in an amount of about 0.5-1.5 grams/serving, about 0.75-1.25 grams/serving, or about 0.9-1.1 grams/serving, or about 1.0 gram/serving, where the serving size is 36-38 grams/serving (or 24 fluid ounces/serving). Alternatively, glutamine may be present in the composition in an amount of about 2 to about 3.5 weight percent, about 2.5-3.25 weight percent, about 2.75-3.0 weight percent, or about 3 weight percent of the composition.

Taurine is also present in the composition in an amount of about 0.1-0.2 grams/serving, about 0.125-0.175 grams/serving, or about 0.15-0.16 grams/serving, where the serving size is 36-38 grams/serving (or 24 fluid ounces/serving).

Alternatively, taurine may be present in an amount of about 0.2-0.5 weight percent, about 0.3-0.45 weight percent, or about 0.4-0.42 weight percent of the composition. The combination of collagen with glutamine and taurine is believed to provide the enhanced uptake of collagen by the recipient.

In the present invention, the composition may contain one or more of the nine essential amino acids, branched-chain amino acids, and naturally occurring amino acids.

In one embodiment, the composition of the present invention include the presence of the nine essential amino acids. The nine essential amino acids are leucine, isoleucine, valine, lysine, phenylalanine, threonine, tryptophan, histidine, and methionine. The total amount of these essential amino acids (EAA) in the composition may vary, but, in a 36-38 grams (or 24 fluid ounce) serving size, the EAAs may be present in an amount of about 4-10 grams/serving, about 6.5-9.0 grams/serving, about 7-8 grams/serving, about 5 grams/serving, about 6 grams/serving, about 7 grams/serving, about 8 grams/serving, or about 9 grams/serving. Alternatively the total amount of the EAAs may be present in an amount of about 15-24, 16-20, about 17-20, about 17, about 18, about 19, about 20, or about 21 weight percent of the total composition. Individually, each essential amino acid may be present in varying amounts, such as about 0.01-3 grams/serving in a 36-38 grams serving size. Alternatively, each essential amino acid may be present in an amount of about 0.06-8.5 weight percent of the total composition.

The amino acid profile of the composition may include naturally occurring amino acids and branched-chain amino acids. For example, branched-chain amino acids (BCAAs) may include, but are not limited to, the essential amino acids of isoleucine, leucine, and valine. In one embodiment, BCAAs make up about 3-6 grams/serving or about 5 grams/serving of the composition, where the serving size is 36-38 grams/service (or 24 fluid ounces/serving). Naturally occurring amino acids that may be included in the composition include, but are not limited to, alanine, arginine, aspartic acid, glutamic acid, glycine, histidine, hydroxylysine, hydroxyproline, isoleucine, leucine, lysine, methionine, phenylalanine, proline, serine, threonine, trypophan, tyrosine, and valine. In some embodiments, the naturally occurring amino acids may or may not be used in the present invention.

In an embodiment of the present invention, a blend of one or more of the nine essential amino acids, branched-chain amino acids, and naturally occurring amino acids is present in the composition in an amount of 4-12 grams/serving, at least 5-5.5 grams/serving, about 7-10 grams/serving, about 4 grams/serving, about 4.5 grams/serving, about 5 grams/serving, or about 6 grams/serving, where the serving size is 36-38 grams/serving (or 24 fluid ounces/serving).

Additional nutrients may be used in the composition including electrolytes, vitamins, minerals, and other dietary supplements. Suitable electrolytes include, but are not limited to, sodium, potassium, magnesium, calcium, bicarbonate, chloride, and phosphate. The total amount of electrolytes may be added to the composition in an amount of about 0.25-4.0 weight percent of the composition, about 1.0-3.8, or about 1.5.2-3.5 weight percent of the composition. Alternatively, the total electrolytes may be present in a range of about 0.1 to 1.5 grams/serving, about 0.5 to 1.25 grams/serving, about 0.75 to 1.1 grams/serving, or about 0.8 to 1.1 grams/serving, where the serving size is 36-38 grams/serving (or 24 fluid ounces/serving). Sodium may be present in any form, such as sea salt, iodized salt, Himalayan pink sea salt, in an amount of about 0.20-0.325 grams/serving or 0.25-0.30 grams/serving, where the serving size is 36-38 grams/serving (or 24 fluid ounces/serving). Alternatively, sodium may be present in a range of about 0.5-1.0 weight percent or about 0.6-0.9 weight percent of the total composition. Potassium may be present in any suitable form, such as a potassium citrate, potassium chloride, potassium sorbate, or the like. Potassium may be present in an amount of about 0.05-0.25 grams/serving or about 0.1-0.2 grams/serving, where the serving size is 36-38 grams/serving. Alternatively, potassium may be present in a range of about 0.4-0.8 or about 0.5-0.7 weight percent of the total composition. Magnesium may be present in any suitable form, such as a potassium citrate. Magnesium may be present may in an amount of about 0.05-0.2 grams/serving or about 0.075-0.125 grams/serving, where the serving size is 36-38 grams/serving (or 24 fluid ounces/serving). Alternatively, magnesium may be present in a range of about 0.1-0.6 or about 0.2-0.4 weight percent of the total composition. Zinc may be present in any suitable form, such as a zinc sulfate. Zinc may be present in an amount of about 0.001-0.02 grams/serving or about 0.002-0.004 grams/serving, where the serving size is 36-38 grams/serving (or 24 fluid ounces/serving). Alternatively, zinc may be present in a range of or about 0.002-0.06 or about 0.005-0.01 weight percent of the total composition.

In addition, certain minerals and elements may be added to the composition as a dietary supplement. For example, selenium and thiamine are appropriate for use in the composition. Selenium may be present in any suitable form, such as a sodium selenium. Selenium may be present in the composition in an amount of about 0.00001-0.0001 grams/serving, about 0.000015-0.000075 grams/serving, or about 0.00002-0.00004 grams/serving, where the serving size is 36-38 grams/serving (or 24 fluid ounces/serving). Alternatively, selenium may be present in a range of about 0.00002-0.0003, about 0.00004-0.0002, or about 0.00005-0.0001 weight percent of the total composition. Thiamine is a mineral that may be present in any suitable form, such as thiamine HCl. Thiamine may be present in the composition in an amount of about 0.0004-0.002 grams/serving, about 0.0009-0.001 grams/serving, or about 0.0009-0.004 grams/serving, where the serving size is 36-38 grams/serving (or 24 fluid ounces/serving). Alternatively, thiamine may be present in a range of about 0.001-0.003, or about 0.0025-0.003 weight percent of the total composition.

Vitamins may further be added to the composition. Any vitamins suitable for ingestion in a dietary supplement is suitable for use. Suitable vitamins include but are not limited to Vitamin B, including Vitamin B1 (e.g., as thiamine chloride), Vitamin B2 (e.g., as riboflavin), Vitamin B3 (e.g., niacinamide), Vitamin B6 (e.g., as pyridoxine HCl), Vitamin B5 (e.g., as pantothenic acid or D-calcium pantothenate), and folate (e.g., as folic acid PWD), Vitamin C (e.g., as sodium ascorbate), Vitamin D, Vitamin E, etc. In the context of the present invention, each of the vitamins may be independently present in the composition in an amount of about 0-0.2 grams/serving, about 0-1 grams/serving, about 0.2-0.8 grams/serving, or about 0.4-0.6 grams/serving, where the serving size is 36-38 grams/serving (or 24 fluid ounces/serving). Alternatively, each vitamin may be present in a range of about 0-0.25, about 0-0.2, about 0.001-0.2, or about 0.002-0.175 weight percent of the total composition.

Moreover, the composition may be flavored using any known natural flavors to enhance the flavor of the composition. Additionally, other additives suitable for dietary supplements, including but not limited to, coconut water powder, malic acid, monk fruit extract, and fruit and vegetable juice powder (for color).

In accordance with the present invention, suitable compositions include, but are not limited, to those described in Tables 1 and 2:

TABLE 1

Nutritional information on five powder compositions (Powder 1, Powder 2, Powder 3, Powder 4, and Powder 5 of the present invention:

|  | Powder 1 38 g/serving Amount per serving | Powder 2 36 g/serving Amount per serving | Powder 3 38 g/serving Amount per serving | Powder 4 36 g/serving Amount per serving | Powder 5 38 g/serving Amount per serving |
|---|---|---|---|---|---|
| Calories | 100 | 100 | 100 | 100 | 100 |
| Total Carbohydrate | 6 g | 6 g | 6 g | 6 g | 6 g |
| Total Sugars | 4 g | 4 g | 4 g | 4 g | 4 g |
| Protein | 18 g | 18 g | 18 g | 18 g | 18 g |
| Vitamin C | 45 mg | 45 mg | 45 mg | 45 mg | 45 mg |
| Thiamin | 0.6 mg | 0.6 mg | 0.6 mg | 0.6 mg | 0.6 mg |
| Riboflavin | 0.65 mg | 0.65 mg | 0.65 mg | 0.65 mg | 0.65 mg |
| Niacin | 8 mg NE | 8 mg NE | 8 mg NE | 8 mg NE | 8 mg NE |
| Vitamin B6 | 0.85 mg | 0.85 mg | 0.85 mg | 0.85 mg | 0.85 mg |
| Folate | 200 mcg DFE | 200 mcg DFE | 200 mcg DFE | 200 mcg DFE | 200 mcg DFE |
| Magnesium | 105 mg | 105 mg | 105 mg | 105 mg | 105 mg |
| Zinc | 3.5 mg | 3.5 mg | 3.5 mg | 3.5 mg | 3.5 mg |
| Selenium | 27.5 mcg | 27.5 mcg | 27.5 mcg | 27.5 mcg | 27.5 mcg |
| Sodium | 250 mg | 300 mg | 230 mg | 230 mg | 250 mg |
| Potassium | 205 mg | 205 mg | 205 mg | 205 mg | 205 mg |

For each of the powder compositions, Powder 1, Powder, 2, Powder 3, Powder 4, and Powder 5, the following ingredients are present:

| Ingredient | Powder 1 38 g/serving Amount per serving | Powder 2 36 g/serving Amount per serving | Powder 3 38 g/serving Amount per serving | Powder 4 36 g/serving Amount per serving | Powder 5 38 g/serving Amount per serving |
|---|---|---|---|---|---|
| Collagen peptides (from bovine) | 20 g | 20 g | 20 g | 20 g | 20 g |
| L-Glutamine | 970 mg | 970 mg | 970 mg | 970 mg | 970 mg |
| Taurine | 135 mg | 135 mg | 135 mg | 135 mg | 135 mg |
| Vital Proteins EAA Blend (from collagen peptides and individual amino acids) L-leucine, L-isoleucine, L-lysine, L-phenylalanine, L-threonine, L-tryptophan, L-histidine, L-methionine | 8 g | 8 g | 8 g | 8 g | 8 g |

TABLE 2

Nutritional information on ready-to-drink compositions (RTD 1, RTD 2, and RTD 3) of the present invention.

|  | RTD 1 24 fl oz/serving Amount per serving | RTD 2 24 fl oz/serving Amount per serving | RTD 3 24 fl oz/serving Amount per serving |
|---|---|---|---|
| Calories | 100 | 100 | 100 |
| Total Carbohydrate | 8 g | 6 g | 6 g |
| Total Sugars | 5 g | 5 g | 5 g |
| Protein | 18 g | 18 g | 18 g |
| Vitamin C | 45 mg | 45 mg | 45 mg |
| Thiamin | 0.6 mg | 0.6 mg | 0.6 mg |
| Riboflavin | 0.65 mg | 0.65 mg | 0.65 mg |
| Niacin | 8 mg NE | 8 mg NE | 8 mg NE |
| Vitamin B6 | 0.85 mg | 0.85 mg | 0.85 mg |
| Folate | 200 mcg DFE | 200 mcg DFE | 200 mcg DFE |
| Magnesium | 105 mg | 105 mg | 105 mg |
| Zinc | 3.5 mg | 3.5 mg | 3.5 mg |
| Selenium | 27.5 mcg | 27.5 mcg | 27.5 mcg |
| Sodium | 280 mg | 270 mg | 250 mg |
| Potassium | 200 mg | 200 mg | 200 mg |

For each of the ready-to-drink compositions, RTD 1, RTD 2, and RTD 3, the following ingredients are present:

| Ingredient | RTD 1 (Blackberry Lime) Amount per serving | RTD 2 (Citrus Fruits) Amount per serving | RTD 3 (Yuzu Clementine) Amount per serving |
|---|---|---|---|
| Collagen peptides (from bovine) | 20 g | 20 g | 20 g |
| L-Glutamine | 970 mg | 970 mg | 970 mg |
| Taurine | 135 mg | 135 mg | 135 mg |
| Vital Proteins EAA Blend (from collagen peptides and individual amino acids) L-leucine, L-isoleucine, L-lysine, L-phenylalanine, L-threonine, L-tryptophan, L-histidine, L-methionine | 8 g | 8 g | 8 g |

In an embodiment of the present invention, the following amino acid profile is present:

| Amino Acid | Amount per serving |
|---|---|
| Alanine | 1935 mg |
| Arginine | 1570 mg |
| Aspartic Acid | 1151 mg |
| Glutamic acid | 3071 mg |
| Glycine | 4728 mg |
| Histidine** | 138 mg |
| Hydroxylysine | 40 mg |
| Hydroxyproline | 2302 mg |
| Isoleucine**⁻ | 1093 mg |
| Leucine**⁻ | 2817 mg |
| Lysine** | 1314 mg |
| Methionine** | 149 mg |
| Phenylalanine** | 1053 mg |
| Proline | 2659 mg |
| Serine | 661 mg |
| Threonine** | 690 mg |
| Tryptophan** | 54 mg |
| Tyrosine | 102 mg |
| Valine**⁻ | 1352 mg |

**Essential amino acids
⁻Branched-Chain Amino Acids (BCAAs)

In an embodiment of the present invention, the caloric intake of the supplement is less than about 200 calories, less than about 150 calories, about 125 calories, or about 100 calories per serving. Additionally, the amount of carbohydrates and total sugars in the composition is desirably low. For example, the carbohydrates may be present in an amount of less than 10 grams/serving, less than 8 grams/serving, less than 7 grams/serving, about 6 grams/serving, or about 5 grams/serving. Similarly, the total sugars is desirably kept low, e.g., less than 6 grams/serving, less than 5 grams/serving, about 5 grams/serving, or about 4 grams/serving. As noted above, the content of the protein, in the form of collagen or collagen peptides, is high, preferably above 10 grams/serving, above 15 gram/serving, above 16 grams/serving, above 17 grams/serving, about 18 grams/serving, about 19 grams/serving, or about 20 grams/serving. In another embodiment of the invention, no artificial sweeteners or sugars are added to the composition.

The present invention is expected to increase the collagen levels of the athlete to within 0-5%, 0-10%, or 0-15% of the collagen levels pre-workout. Furthermore, the levels of PD and DPD in the urine of athletes after supplementation with the composition of the present invention is expected to indicate that the PD and DPD levels are similar to pre-workout levels or within 1%, 2%, 5%, or 10% of the pre-workout levels. Moreover, because the present invention utilizes the nine essential amino acids, vitamins, mineral, and electrolyte, the nutrient levels for these nutrients in the body are greatly enhanced relative to pre-workout levels along with the collagen levels.

Powder Examples

Compositions of the powder formulas Powder 1, Powder 2, Powder 3, Powder 4, and Powder 5 depicted in Table 1 were prepared.

RTD Examples

Compositions of the ready-to drink formulas RTD 1, RTD 2, and RTD 3 depicted in Table 2 were prepared.

The invention claimed is:

1. A method of replacing collagen broken down during physical activity in a patient in need thereof, the method comprising:
    following the physical activity, administering to the patient a dietary supplement composition consisting of:
    total sugar in an amount of no greater than 4 grams per serving of the dietary supplement composition;
    collagen in an amount of 17-23 grams per serving of the dietary supplement composition;
    glutamine in an amount of about 0.5-1.5 grams per serving of the dietary supplement composition;
    taurine in an amount of about 0.1-0.2 grams per serving of the dietary supplement composition;
    essential amino acids leucine, isoleucine, valine, lysine, phenylalanine, threonine, tryptophan, histidine, and methionine; and
    optionally at least one additional ingredient selected from the group consisting of carbohydrate, protein, vitamins, electrolytes, minerals, flavors, colors, coconut water powder, malic acid, fruit extract, and combinations thereof,
    wherein the serving of the dietary supplement composition is 36-38 grams or 24 fluid ounces,
    wherein the dietary supplement composition is in a form of either a ready-to-drink liquid or a powder mixed with a liquid prior to administration.

2. A method of replacing collagen broken down during physical activity in a patient in need thereof, the method comprising:
    following the physical activity, administering to the patient a dietary supplement composition consisting of:
    total sugar in an amount of no greater than 4 grams per serving of the dietary supplement composition;
    collagen in an amount of about 20 grams per serving of the dietary supplement composition;
    glutamine in an amount of about 0.97 grams per serving of the dietary supplement composition;
    taurine in an amount of about 0.135 grams per serving of the dietary supplement composition;
    essential amino acids leucine, isoleucine, valine, lysine, phenylalanine, threonine, tryptophan, histidine, and methionine; and
    optionally at least one additional ingredient selected from the group consisting of carbohydrate, protein, vitamins, electrolytes, minerals, flavors, colors, coconut water powder, malic acid, fruit extract, and combinations thereof,
    wherein the serving of the dietary supplement composition is 36-38 grams or 24 fluid ounces,
    wherein the dietary supplement composition is in a form of either a ready-to-drink liquid or a powder mixed with a liquid prior to administration.

3. A method of replacing collagen broken down during physical activity in a patient in need thereof, the method comprising:
    following the physical activity, administering to the patient in need thereof a dietary supplement composition consisting of:

total sugar in an amount of no greater than 4 grams per serving of the dietary supplement composition;
collagen in an amount of 17-23 grams per serving of the dietary supplement composition;
glutamine in an amount of about 0.5-1.5 grams per serving of the dietary supplement composition;
taurine in an amount of about 0.1-0.2 grams per serving of the dietary supplement composition;
essential amino acids leucine, isoleucine, valine, lysine, phenylalanine, threonine, tryptophan, histidine, and methionine; and
optionally at least one additional ingredient selected from the group consisting of carbohydrate, protein, vitamins, electrolytes, minerals, flavors, colors, coconut water powder, malic acid, fruit extract, and combinations thereof,
the essential amino acids in a total amount of about 6-10 grams per serving of the dietary supplement composition,
wherein the serving of the dietary supplement composition is 36-38 grams or 24 fluid ounces,
wherein the dietary supplement composition is in a form of either a ready-to-drink liquid or a powder mixed with a liquid prior to administration.

4. A method of replacing collagen following physical activity in a patient in need thereof, the method comprising administering to the patient a dietary supplement composition consisting of:
an amino acid blend consisting of the following amino acid profile per 36-38 grams or 24 fluid ounces serving of the dietary supplement composition:

| Amino Acid | Amount per serving |
|---|---|
| Alanine | 1935 mg |
| Arginine | 1570 mg |
| Aspartic Acid | 1151 mg |
| Glutamic acid | 3071 mg |
| Glycine | 4728 mg |
| Histidine | 138 mg |
| Hydroxylysine | 40 mg |
| Hydroxyproline | 2302 mg |
| Isoleucine | 1093 mg |
| Leucine | 2817 mg |
| Lysine | 1314 mg |
| Methionine | 149 mg |
| Phenylalanine | 1053 mg |
| Proline | 2659 mg |
| Serine | 661 mg |
| Threonine | 690 mg |
| Tryptophan | 54 mg |
| Tyrosine | 102 mg |
| Valine | 1352 mg; | collagen in an amount of 17-23 grams per serving;
total sugar in an amount of no greater than 4 grams/serving; and
optionally at least one additional ingredient selected from the group consisting of carbohydrate, protein, vitamins, electrolytes, minerals, flavors, colors, coconut water powder, malic acid, fruit extract, and combinations thereof,
wherein the dietary supplement composition is in a form of either a ready-to-drink liquid or a powder mixed with a liquid prior to administration.

5. The method of claim 1, wherein the vitamins are selected from the group consisting of Vitamin B1, Vitamin B2, Vitamin B3, Vitamin B6, Vitamin B5, folate, Vitamin C, Vitamin D, Vitamin E, and combinations thereof.

6. The method of claim 5, wherein the vitamins are Vitamin B1, Vitamin B2, Vitamin B3, Vitamin B6, Vitamin B5, folate and Vitamin C.

7. The method of claim 5, wherein the vitamins are Vitamin B3, Vitamin B6, Vitamin B5 and Vitamin C.

* * * * *